United States Patent
Albright et al.

(10) Patent No.: US 9,289,590 B2
(45) Date of Patent: Mar. 22, 2016

(54) PEELABLE LID FOR CONTAINER WITH MULTI-POINT PEEL SYSTEM

(71) Applicant: Physio-Control, Inc., Redmond, WA (US)

(72) Inventors: Ethan Albright, Mill Creek, WA (US); Ramesh Ammanath, Kirkland, WA (US); Peter Wesley Bristol, Seattle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 14/458,090

(22) Filed: Aug. 12, 2014

(65) Prior Publication Data
US 2015/0045845 A1    Feb. 12, 2015

Related U.S. Application Data

(60) Provisional application No. 61/865,089, filed on Aug. 12, 2013.

(51) Int. Cl.
*A61N 1/04* (2006.01)
*A61B 19/02* (2006.01)
*A61N 1/39* (2006.01)

(52) U.S. Cl.
CPC .............. *A61N 1/046* (2013.01); *A61N 1/3968* (2013.01)

(58) Field of Classification Search
None
See application file for complete search history.

(56) References Cited

U.S. PATENT DOCUMENTS

| | | | |
|---|---|---|---|
| 2003/0167075 A1* | 9/2003 | Fincke | A61N 1/0472 607/8 |
| 2003/0216785 A1* | 11/2003 | Edwards | A61N 1/3993 607/5 |
| 2011/0054553 A1* | 3/2011 | Cordaro | A61N 1/025 607/5 |
| 2014/0012360 A1 | 1/2014 | Griesser | |

FOREIGN PATENT DOCUMENTS

| EP | 2 691 146 | 5/2014 |
|---|---|---|
| WO | 2012/131536 A2 | 10/2012 |

* cited by examiner

*Primary Examiner* — Brian T Gedeon
*Assistant Examiner* — Ankit Tejani
(74) *Attorney, Agent, or Firm* — Marger Johnson

(57) ABSTRACT

A peelable lid system includes a peelable lid, a seal configured to seal the peelable lid to a container, a handle coupled to the peelable lid, and a lifting mechanism coupled to handle. The lifting mechanism can be coupled to the peelable lid at a plurality of attachment points, including at least one attachment point coupled to the peelable lid away from the handle. The lifting mechanism can be configured to lift at least one portion of the peelable lid near each of the plurality of attachment points.

15 Claims, 23 Drawing Sheets

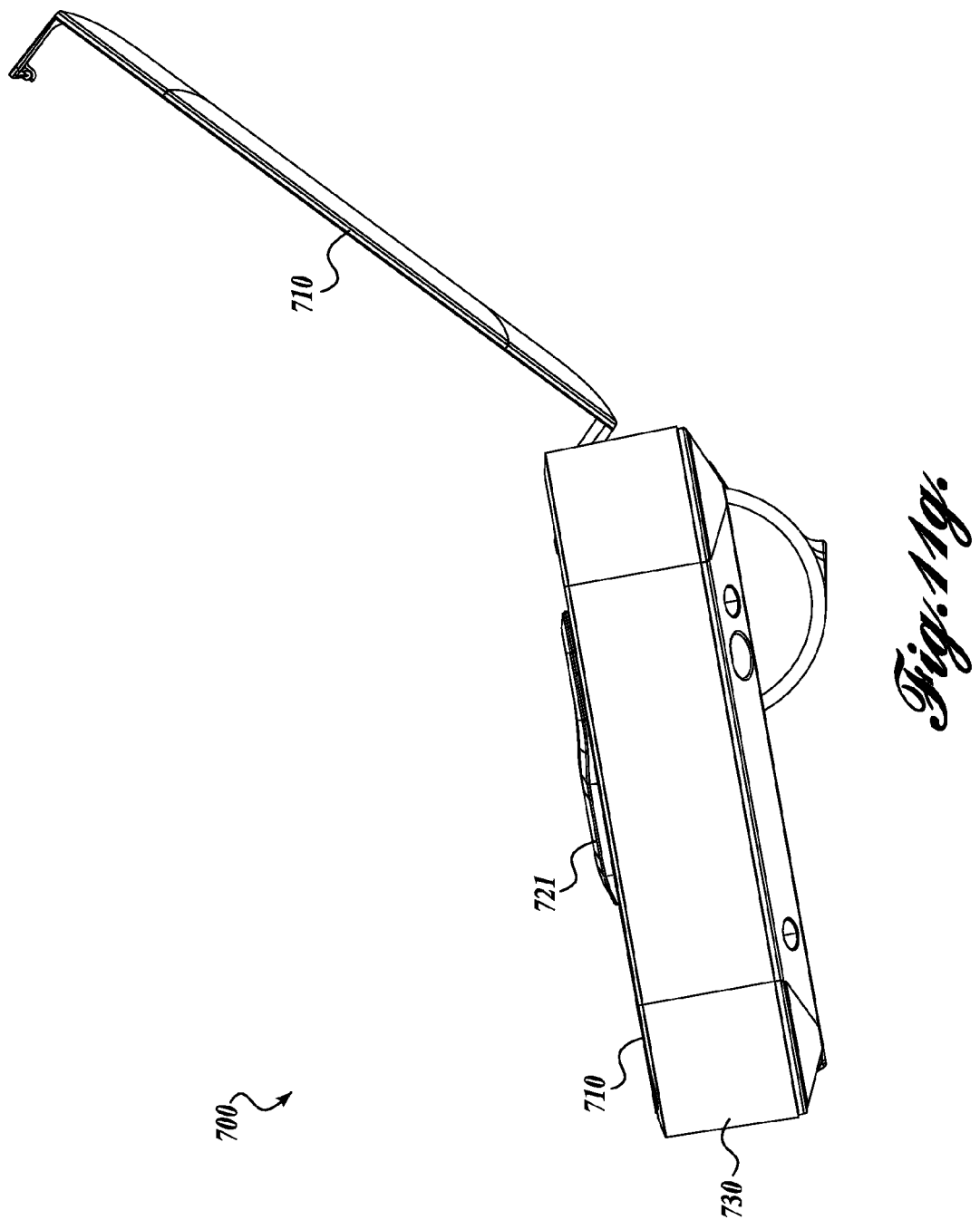

PEELABLE LID FOR CONTAINER WITH MULTI-POINT PEEL SYSTEM

CROSS-REFERENCE TO RELATED APPLICATION

This application claims the benefit of U.S. Provisional Application No. 61/865,089, filed Aug. 12, 2013, the disclosure of which is hereby incorporated by reference herein in its entirety.

BACKGROUND

A container can be sealed with a peelable lid to keep the container sealed until a user is ready to break the seal. To break the seal, the user can pull back on the peelable lid to break the seal and remove the peelable lid. Peelable lids can be used on flexible containers, such as pouch-type or bag-type containers. Flexible containers can be used to contain items, such as electrode pads of automated external defibrillators (AEDs). In this case, a container with a peelable lid can store an electrode pad of an AED. When a user wants to use the electrode pad, the user can pull the peelable lid to break the seal with the container and remove the peelable lid to gain access to the electrode pad. Peelable lids can include features that can assist the user to peel off the lid. For example, a peelable lid can have a pull tab that protrudes out from an edge of the lid. The pull tab can allow a user to more easily grasp the lid and peel the lid back from the location of the pull tab. A peelable lid can also have multiple pull tabs that protrude out from different points along the edge of the lid. The pull tabs can allow a user to more easily grasp the lid at different locations and peel the lid back from one of the pull tab locations at a time. Pull tabs can also be located at other locations, such as on top of the lid. A user can pull a pull tab on the top of a lid upward to remove the lid from the container.

SUMMARY

The following summary is provided to introduce a selection of concepts in a simplified form that are further described below in the Detailed Description. This summary is not intended to identify key features of the claimed subject matter, nor is it intended to be used as an aid in determining the scope of the claimed subject matter.

In at least one embodiment, a peelable lid system can include a container, a peelable lid, and a seal between the container and the peelable lid. The peelable lid system can also include a handle coupled to the peelable lid and a lifting mechanism. The lifting mechanism can be coupled to the handle and coupled to the peelable lid at a plurality of attachment points. One of the plurality of attachment points can be coupled to the peelable lid away from the handle. The lifting mechanism can be configured to lift at least one portion of the peelable lid near each of the plurality of attachment points.

In one example, the plurality of attachment points can include a first attachment point coupled to a first corner of the peelable lid and a second attachment point coupled to a second corner of the peelable lid. The handle can be coupled to a side of the peelable lid between the first corner and the second corner of the peelable lid. The lifting mechanism can be configured such that, when the pull force is applied to the handle, the first attachment point and the second attachment point are biased away from the container to curl the side of the peelable lid between the first corner and the second corner.

In another example, the at least one of the plurality of attachment points of the lifting mechanism is coupled to the peelable lid near a corner of the peelable lid. The seal can include a corner near the corner of the peelable lid, where the at least one portion of the peelable lid is lifted by the at least one of the plurality of attachment points at the corner of the peelable lid, and where the corner of the seal is broken when the corner of the peelable lid is lifted by the at least one of the plurality of attachment points. The seal can include a rounded corner near the corner of the peelable lid, where the at least one portion of the peelable lid is lifted by the at least one of the plurality of attachment points at the corner of the peelable lid, and where the rounded corner of the seal is broken when the corner of the peelable lid is lifted by the at least one of the plurality of attachment points.

In another example, the peelable lid has a round edge and the seal is round. The handle can be coupled to a first location of the round edge, where the at least one of the plurality of attachment points is coupled to a second location of the round edge, and where a portion of the lifting mechanism between the handle and the at least one of the plurality of attachment points is located along the round edge between the first location and the second location. In other examples, the seal can include one or more of an adhesive, glue, epoxy, a mechanical bond, or a polymer bond, and the container can include one or more of a rigid container or a compliant container. The lifting mechanism can also be configured such that the pull force is transferred to the seal in at least two different locations.

In another embodiment, a peelable lid can include a lid configured to cover an opening of a container, a handle coupled to the seal, and a lifting mechanism coupled to handle. The lifting mechanism can include at least one attachment point coupled to the peelable lid away from the handle. In response to a pull force being applied to the handle when the lid is sealed to the container, the lifting mechanism is configured to lift at least one portion of the lid near the at least one attachment point.

In one example, the lifting mechanism comprises a compliant mechanism. The compliant mechanism can be integrally formed with the handle. In another example, the lifting mechanism comprises a plurality of links coupled via at least one pivot joint. The plurality of links can include a first link coupled to the handle and a second link comprising the at least one attachment point. The first link and the second link can be coupled via a first pivot joint. The plurality of links can also include a third link coupled to the first link via a second pivot joint.

In another example, the lifting mechanism can be configured such that the pull force can be transferred to the seal at a first location in a first direction that is different from a second direction of the pull force transferred to the seal at a second location. The first direction can be substantially perpendicular to a side of the lid, and the second direction can be not substantially perpendicular to the side of the lid. In another example, the lid can include one or more layers that can include at least one of a paper layer, a wax layer, a metallic foil, or a polymer film.

DESCRIPTION OF THE DRAWINGS

FIGS. 11A to 11G depict, respectively, a perspective view, a front view, a back view, a top view, a bottom view, a right side view, and a left side view of an embodiment of an automated external defibrillator (AED) with a cover in an opened position.

DETAILED DESCRIPTION

Figure 1:
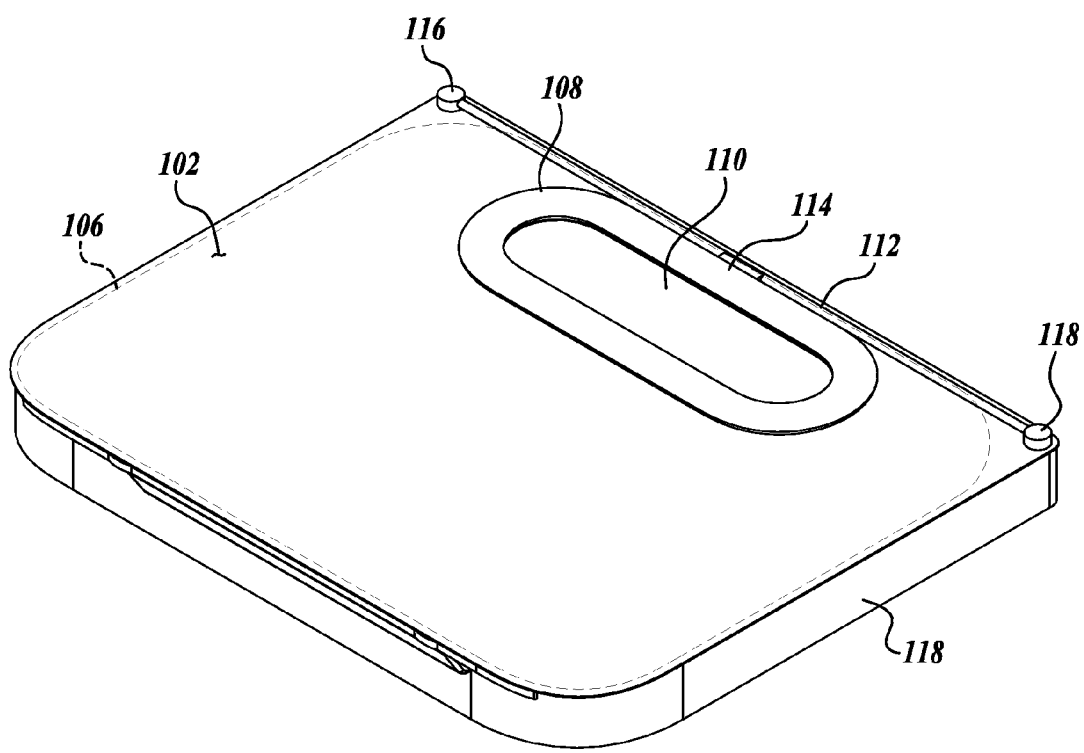
FIG. 1 depicts a perspective view of an embodiment of a system with a peelable lid on a container, where a handle and a lifting mechanism of the peelable lid are at rest.

Removing peelable container lids by pulling on a pull tab can pose a number of problems. In one example, as a user pulls a pull tab of a peelable container lid, the pull force can cause the lid to tear near the pull tab. Such a tear can result in the pull tab being removed from the rest of the lid or otherwise rendered inoperable while a portion of the lid remains attached to the container. The user can remove the remaining portion of the lid; however, this extra step can add to the time and complexity required to remove the entire lid from the container. Tearing can be particularly problematic where a strong adhesive is used to seal the lid to the container. A strong adhesive can require greater pull force to peel back the lid, increasing the possibility that the pull force will exceed the tensile strength of the pull tab material and/or lid material before the lid is properly peeled back from the container.

In another example, pull tabs on peelable container lids are typically designed to be pulled in a specific direction to properly peel the lid off the container. A pull tab on a round lid can be designed to be pulled toward the center of the lid. Similarly, a pull tab on a corner of a rectangular lid can be designed to be pulled diagonally across the lid. Because the pull tab is designed to be pulled in one direction, the container may need to be reoriented for a user to be able to properly pull the pull tab. However, there are times when the container cannot be easily reoriented or when pulling a particular direction is not convenient for the user. For example, it may be desirable to allow a user to pull from a side of a rectangular lid, but the strength of the adhesive between the lid and the container is typically too great for a pull tab to be pulled perpendicular to the side.

To address some of the problems with traditional peelable lids, a peelable lid handle can be provided that transmits pull force on the handle to pull force at two or more different locations along the lid. FIGS. 1 to 4 depict an example of a peelable lid system that has a peelable lid 102 covering an opening of a container 104. The peelable lid 102 can be made out any number of materials, such as paper, wax, metallic foils, polymer films, and the like. In some cases, the peelable lid 102 can have multiple layers, such as a layer of wax over a metallic film layer and a layer of paper over the layer of wax. Any number of other materials and/or combination of materials can be used to form the peelable lid 102. The peelable lid 102 can be sealed to the container 104 via a seal 106, as indicated by dashed lines in the figures.

The container 104 can be a rigid container, such as a hard plastic container, a metal container, and the like. The container 104 can also be a compliant container, such as a paper or plastic packet, a flexible plastic, and the like. The seal 106 can be made using an adhesive, such as glue, epoxy, or any other type of adhesive. The seal 106 can also be a physical bond, such as a polymer bond that has been created by melting a polymer onto the container.

In one example, the peelable lid 102 can have a metallic foil layer and a polymer layer. To create the seal, the metallic foil layer can be heated which causes the polymer layer to also heat up. Some of the polymer from the heated polymer layer can flow from the lid 102 onto the container 104. When the polymer layer cools, the polymer from the polymer layer forms a bond between the lid 102 and the container 104.

A handle 108 can be coupled to the lid 102. The handle 108 can be made of any type of material, including rigid materials and/or compliant materials. In the embodiment shown in FIGS. 1 to 4, the handle 108 can include a hole 110 that aids a user in grasping the handle 108. However, the handle 108 can have any other form, such as the form of a pull tab without a hole.

The handle 108 can be coupled to a lifting mechanism 112. In some embodiments, the lifting mechanism 112 can be an integrally-formed part of the handle 108. In other embodiments, the lifting mechanism 112 can be a separate part that is coupled to the handle 108. In the embodiment shown in FIGS. 1 to 4, the lifting mechanism 112 is a compliant mechanism. In other embodiments, the lifting mechanism 112 can have rigid segments connected via pivot joints, such as a three-bar linkage, as discussed in greater detail below. The handle 108 can have a color that is different from a color of the lid 102 and/or the container 104. For example, a handle 108 that is brighter in color than the lid 102 and/or the container 104 (e.g., an orange or yellow handle 108 with a gray or white lid 102) can provide a user with a visual cue that the lid 102 can be opened by pulling on the handle 108. Such a visual cue can help in speeding the process of a user to identify the handle 108 and in reducing the likelihood of user error in peeling back the lid 102.

The handle 108 can be coupled to the lid 102 in one location. The lifting mechanism 112 can be coupled to the lid 102 in at least one other location. The lifting mechanism can be coupled to the lid 102 using any type of fastener or fastening material, such as a rivet, a snap, or an adhesive. In the embodiment depicted in FIGS. 1 to 4, lifting mechanism 112 is coupled to the lid 102 at two locations: a first attachment point 116 of the lifting mechanism 112 and a second attachment point 118 of the lifting mechanism 112.

Figure 2:
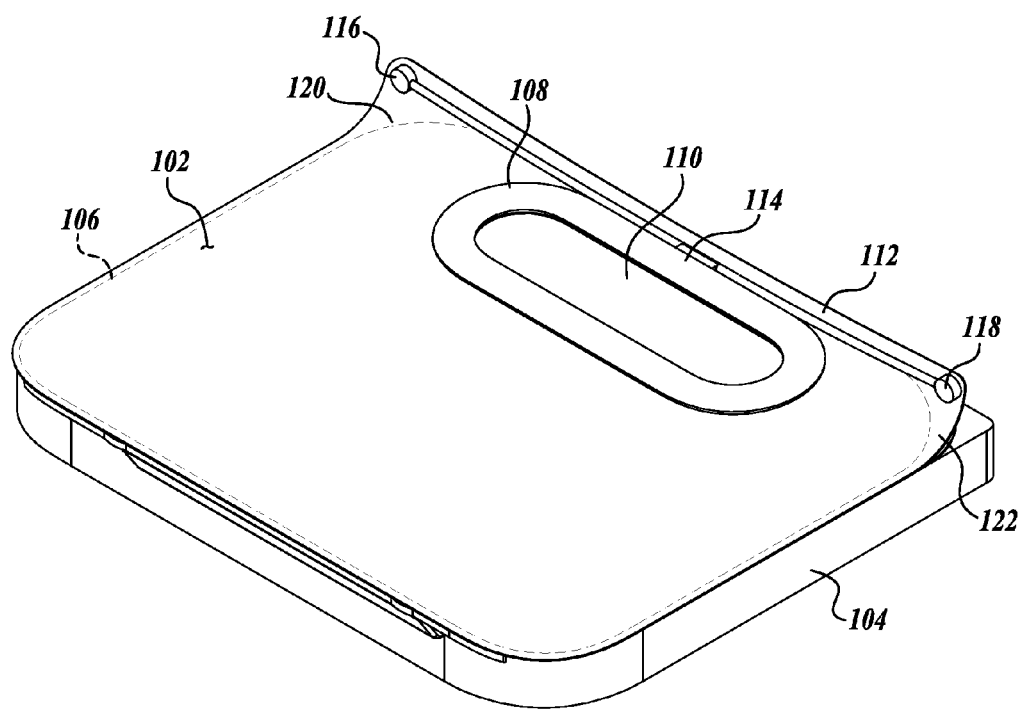
FIG. 2 depicts another perspective view of the embodiment of the system depicted in FIG. 1 with a pull force being exerted on the handle of the peelable lid.

The handle 108 can be pulled to break the seal 106 and peel the lid 102 away from the container 104. Because the handle 108 is coupled to the lid 102 at a first location 114, a pull force on the handle 108 will be transferred to a pull force at the first location 114 along the seal 106. In the embodiment depicted in FIGS. 1 to 4, the first location 114 is along a side of the lid 102. The first location 114 can be a point location on the side of the lid 102 or a particular length along the side of the lid 102. The lifting mechanism 112 can be configured such that, when a pull force is exerted on the handle 108, the first end 116 and the second attachment point 118 of the lifting mechanism 112 are biased away from the container 104. As shown in FIG. 2, the biasing of the first attachment point 116 and the second attachment point 118 causes the lid 102 to be lifted away from the container 104 and the points where the first attachment point 116 and the second attachment point 118 are coupled to the lid 102. The lifting of the lid 102 transfers the pull force of the handle 108 to a second location 120 along the seal 106 and a third location 122 along the seal 106. Thus, as shown in FIG. 2, as the handle 108 is pulled, the pull force is transferred to the first location 114, the second location 120, and the third location 122.

Figure 3:
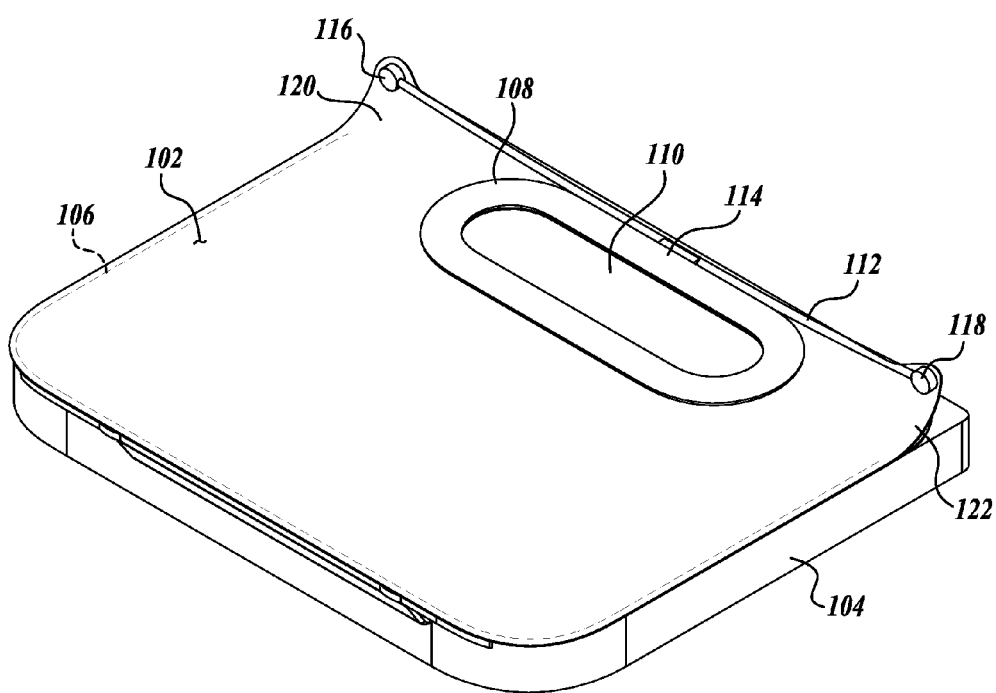
FIG. 3 depicts another perspective view of the embodiment of the system depicted in FIG. 1 with the handle of the peelable lid pulled back to partially remove the peelable lid from the container.
Figure 4:
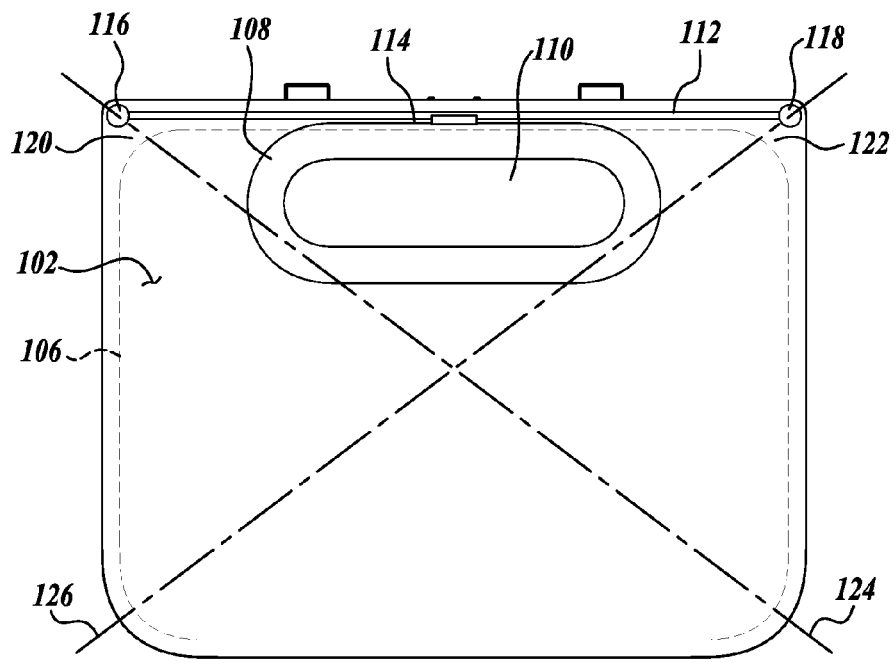
FIG. 4 depicts a top view of the embodiment of the system depicted in FIG. 1.

As shown in FIG. 3, the lid 102 will begin to peel from the container 104 as the pull force continues to be exerted on the handle 108. The lifting mechanism 112 can continue to bend such that the side of the lid 102 is peeled from the container 104 at the second location 120 and the third location 122. This bending motion can cause the seal 106 to break starting at each of the second location 120 and the third location 122. The breaks in the seal 106 can progress from the second location 120 toward the first location 114 and from the third location 122 toward the first location 114. The pull force can also cause the seal 106 to break at the first location 114. The breaking of the seal 106 at multiple locations makes it easier for a user to peel the lid 102 back from the container 104. In one example, the user can pull the handle 108 with one hand in one direction while pull force is transferred to multiple points along the seal 106 to begin peeling the lid 102 from multiple locations. Once the lid 102 begins peeling back from the container 104, as shown in FIG. 3, the user can continue pulling the handle 108 until the lid 102 is completely peeled off of the container 104.

The combination of the lifting mechanism 112 and the handle 108 allows for the handle 108 to be pulled in a direction that the lid 102 could not easily be peeled without the aid of the lifting mechanism 112. For example, if the embodiment depicted in FIGS. 1 to 4 did not include the lifting mechanism 112, it would be difficult for a user to start peeling the lid 102 from the container 104 by pulling the handle 108 in a direction perpendicular to the side of the lid 102. With the lifting mechanism 112 in the embodiment depicted in FIGS. 1 to 4, pulling the handle 108 perpendicular to the side of the lid 102 results in a pull force at each of the first location 114, the second location 120, and the third location 122. At the first location 114, the pull force may be substantially perpendicular to the side, but the pull force at the second location 120 and the third location 120 can be in a non-perpendicular direction, as in shown in FIG. 4. For example, the pull force at the second location 120 can be in a first direction 124 that runs substantially diagonal across the lid 102. In another example, the pull force at the third location 122 can be in a second direction 126 that runs substantially diagonal across the lid 102. The pull force at the second location 120 and the third location 120 can be in other directions that are not perpendicular to the side of the lid 102.

In practice, the pull force at the second location 120 and the pull force at the third location 122 can cause the lid 102 to begin peeling at the second location 120 and the third location 122 before the lid 102 begins to peel from the first location 114. If the lid 102 begins to peel from the second location 120 and the third location 122 before peeling at the first location 114, the force that would be required to begin peeing the lid from the first location 114 can be lower than the force required to begin peeling the lid 102 at the first location 114 without the aid of the lifting mechanism 114.

Having the option to pull the lid 102 in one direction (e.g., substantially perpendicular to the lid 102) while causing the lid 102 to peel in a different direction (e.g., in diagonal directions 124 and 126) can reduce the need for a user to reorient the container 104 to peel the lid 102 off of the container 104. For example, it may be difficult or inconvenient for a user to pull from a corner of the lid 102. Being able to remove the lid 102 by pulling the handle 108 from the side of the lid 102 can prevent a user from having to reorient the container 104 to be able to pull from a corner of the lid 102. Moreover, being able to cause pull force at multiple locations along the seal 106 with one action of pulling the handle 108 can add to the speed with which the lid 102 is removed from the container 104. The speed with which a lid 102 is removed from the container 104 can be important in certain instances, such as in the case of removing a peelable lid that covers an electrode tray of an automated external defibrillator (AED), as is described in U.S. patent application Ser. No. 14/457,942, filed herewith, the contents of which are hereby incorporated by reference in their entirety.

Figure 5:
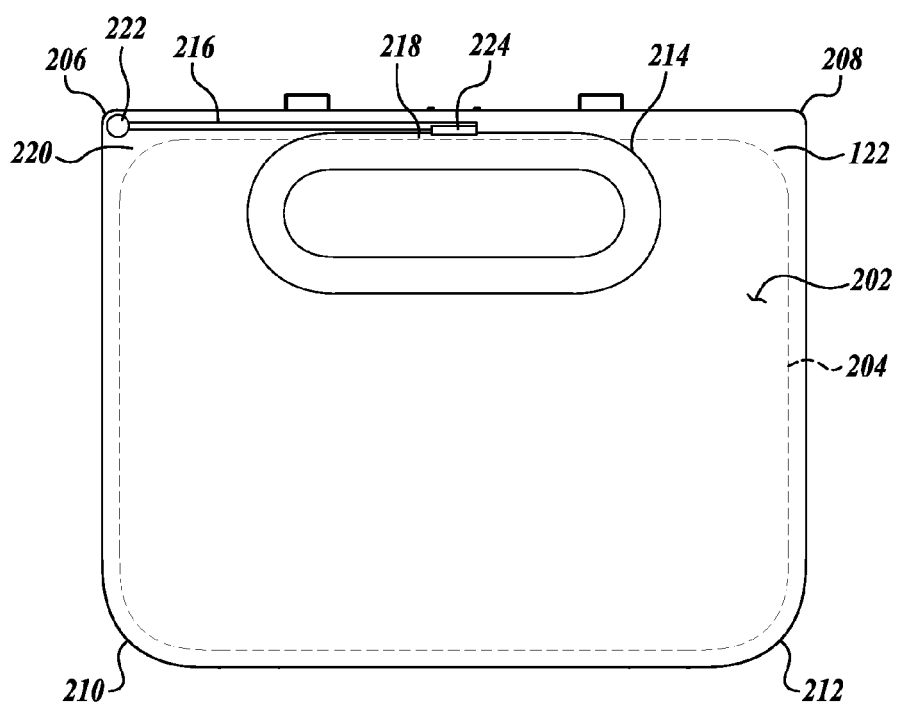
FIG. 5 depicts a top view of an embodiment of a system with a container having a peelable lid with a handle and a lifting mechanism.

In the particular situation with an AED, users typically use an AED in emergency situations, such as when a patient is undergoing a cardiac arrhythmia. In such cases, reducing the time of administering AED treatment increases the probability that the patient will survive and the probability that the patient will not experience significant injury. Users are typically experiencing some level of stress and urgency in these situations. Thus, the ability to remove peelable lids from AED components (e.g., electrode trays, electrode pads, etc.) easily, efficiently, and completely provides a significant advantage in AED treatment. Moreover, it can be advantageous to use seals with certain AED components. Self-adhesive AED electrode pads typically include a gel that functions to adhere the electrode pads to the user's chest and to establish an electrical connection between the electrodes on the electrode pads and the user's chest. The gel on AED electrode pads can dry out over time, rendering the AED electrode pads ineffective or completely unusable. To reduce the speed of gel drying out on AED electrode pads, the electrode and gel side of many AED electrode pads are sealed before they are used. AEDs can include an electrode tray that houses the AED electrode pads, and the entire electrode tray can be sealed to further reduce the speed of gel drying out on AED electrode pads. Peelable lids can come in any number of other arrangements or forms. FIGS. 5 to 8 depict some embodiments of peelable lids. FIG. 5 depicts a top view of an embodiment of a lid 202 that is sealed to a container (not shown) via a seal 204. The lid 202 has a generally rectangular shape. A first corner 206 and a second corner 208 of the lid 202 are square and a third corner 210 and a forth corner 212 of the lid are rounded. The seal 204 is also substantially rectangular in shape with rounded corners. Coupled to the lid 202 are a handle 214 and a lifting mechanism 216. In the embodiment depicted in FIG. 5, the lifting mechanism 216 extends from the handle 214 to a first attachment point 222 near the first corner 206 but does not extend from the handle 214 to the second corner 208. The lifting mechanism 216 is also attached to the lid 202 at a second attachment point 224 near the handle 214. When the handle 214 is pulled, the end of the lifting mechanism 216 near the first corner 206 is biased away from the container. In this way, the pull force on the handle 214 is transferred to a pull force at a first location 218 on the seal 204 near the handle 214 and to a pull force at a second location 220 on the seal 204 near the first corner 206. Even though the lifting mechanism 216 does not extend to second corner 208, pulling the handle 214 still results a pull force at multiple locations: the first location 218 and the second location 220.

Figure 6:
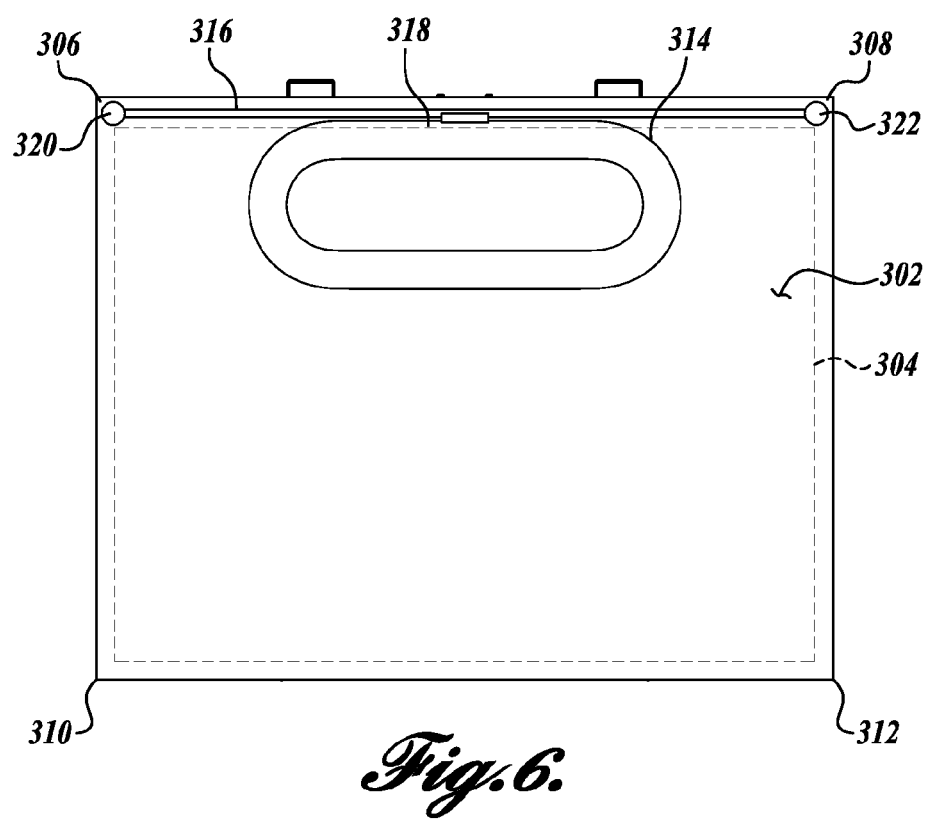
FIG. 6 depicts a top view of an embodiment of a system with a container having a rectangular peelable lid with a handle and a lifting mechanism.

FIG. 6 depicts a top view of an embodiment of a lid 302 that is sealed to a container (not shown) via a seal 304. The lid 302 has a generally rectangular shape with a first corner 306, a second corner 308, a third corner 310, and a fourth corner 312 that are square. The seal 304 is also substantially rectangular in shape with square corners. Coupled to the lid 302 are a handle 314 and a lifting mechanism 316. The lifting mechanism 316 is coupled to the lid 302 at a first attachment point 320 and a second attachment point 322. In the embodiment depicted in FIG. 6, the lifting mechanism 316 extends from the first attachment point 320 near the first corner 306 to the second attachment point 322 near the second corner 308. When the handle 314 is pulled, the end of the lifting mechanism 316 near the first corner 306 is biased away from the container. In this way, the pull force on the handle 314 is transferred to a pull force at a first location 318 on the seal 304 near the handle 314, to a pull force at a second location on the seal 304 near the first corner 306, and to a pull force at a third location on the seal 304 near the second corner 308.

It can be easier to break a seal between a lid and a container at a location where the seal comes to a corner than at other locations, such as at a straight portion (e.g., the first location 218 on seal 204 in FIG. 5) or at a curved portion (e.g., the second location 220 on seal 204). Some peelable lids, such as the lid 202, have a square corner, such as the first corner 206, when the seal under the square corner is rounded, such as the portion of the seal 204 at location 220. This configuration allows a user to better grasp the first corner 206 to use it as a pull tab to peel back the lid 202.

In the embodiment shown in FIG. 6, the seal 304 near the first corner 306 has a square corner. Since the lifting mechanism 316 lifts the corner 306 when the handle 314 is pulled, there is no need for the user to be able to better grasp the first corner 306 to use it as a pull tab. Thus, there is no drawback to the seal 304 having a square corner near the first corner 306. In addition, having a square corner on the seal 304 near the first corner 306 can be easier to break than a rounded corner at the same location.

Figure 7:
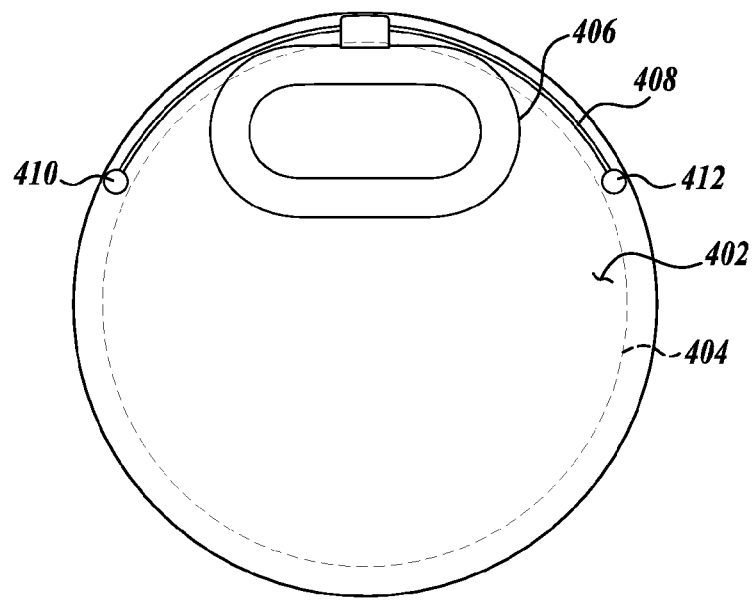
FIG. 7 depicts a top view of an embodiment of a system with a container having a round peelable lid with a handle and a lifting mechanism.

FIG. 7 depicts a top view of an embodiment of a lid 402 that is sealed to a container (not shown) via a seal 404. The lid 402 has a generally round shape. While the particular embodiment of the lid 402 is a circle, other round shapes are possible, such as ovals, ellipses, irregular round shapes, and the like. The seal 404 also has a generally round shape. Coupled to the lid 402 are a handle 406 and a lifting mechanism 408. In the embodiment depicted in FIG. 7, the lifting mechanism 408 is coupled to the lid 402 at a first attachment point 410 and a second attachment point 412. The lifting mechanism 408 is located along the edge of the lid 402 between the first attachment point 410 and the second attachment point 412. When the handle 406 is pulled, the first attachment point 410 and the second attachment point 412 of the lifting mechanism 408 are biased away from the container. In this way, the pull force on the handle 406 is transferred to a pull force at a first location on the seal 404 near the handle 406, to a pull force at a second location on the seal 404 near the first attachment point 410 of the lifting mechanism 408, and to a pull force at a third location on the seal 404 near the second attachment point 412 of the lifting mechanism 408.

Figure 8:
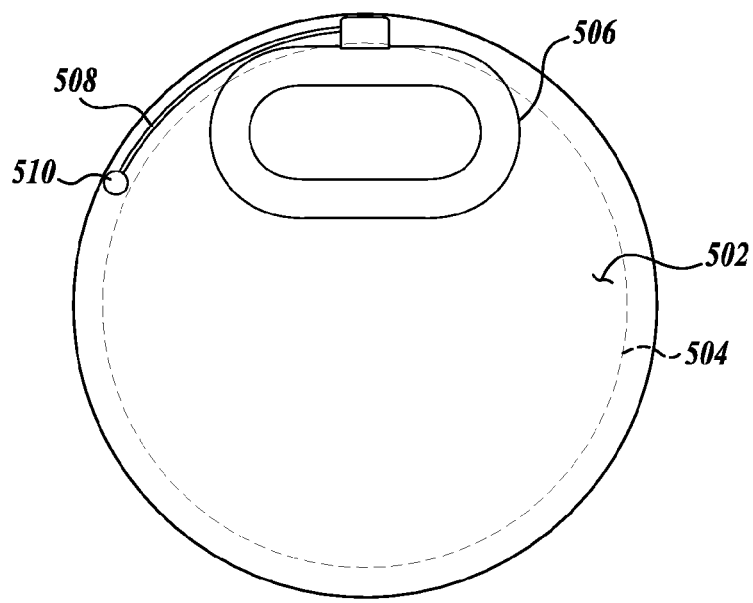
FIG. 8 depicts a top view of another embodiment of a system with a container having a round peelable lid with a handle and a lifting mechanism.

FIG. 8 depicts a top view of an embodiment of a lid 502 that is sealed to a container (not shown) via a seal 504. The lid 502 has a generally round shape. While the particular embodiment of the lid 502 is a circle, other round shapes are possible, such as ovals, ellipses, irregular round shapes, and the like. The seal 504 also has a generally round shape. Coupled to the lid 502 are a handle 506 and a lifting mechanism 508. In the embodiment depicted in FIG. 8, the lifting mechanism 508 is coupled to the lid 502 at a first attachment point 510. The lifting mechanism 508 is located along the edge of the lid 502 between the first end 510 and the handle 506. When the handle 506 is pulled, the first attachment point 510 of the lifting mechanism 508 is biased away from the container. In this way, the pull force on the handle 506 is transferred to a pull force at a first location on the seal 504 near the handle 506 and to a pull force at a second location on the seal 504 near the first attachment point 510 of the lifting mechanism 508.

Figure 9:
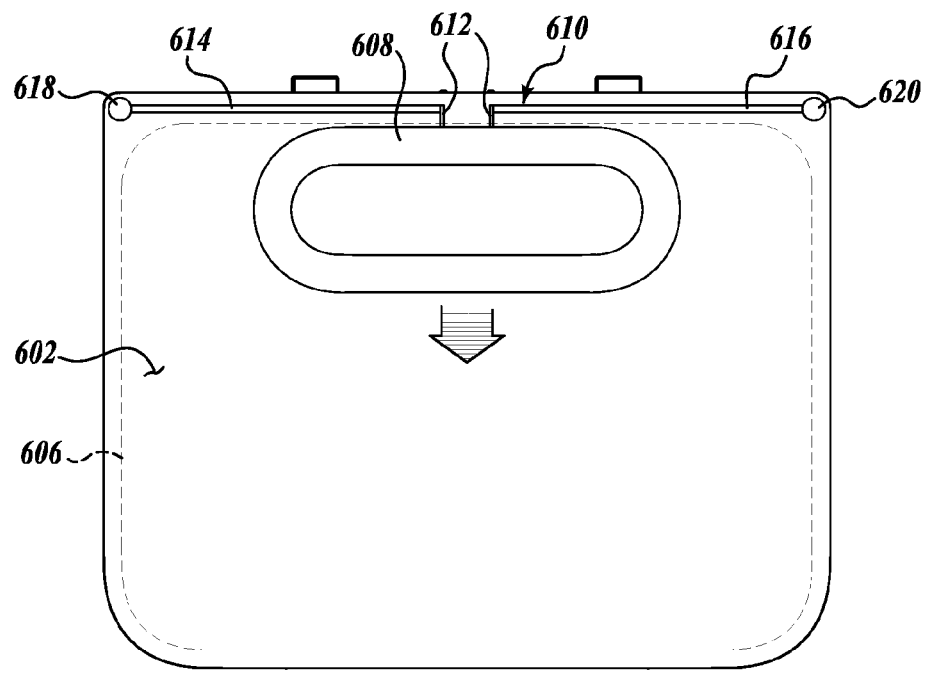
FIG. 9 depicts a perspective view of an embodiment of a system with a container having a round peelable lid with a handle and a three-bar-linkage lifting mechanism, where the handle and the three-bar-linkage lifting mechanism are at rest.
Figure 10:
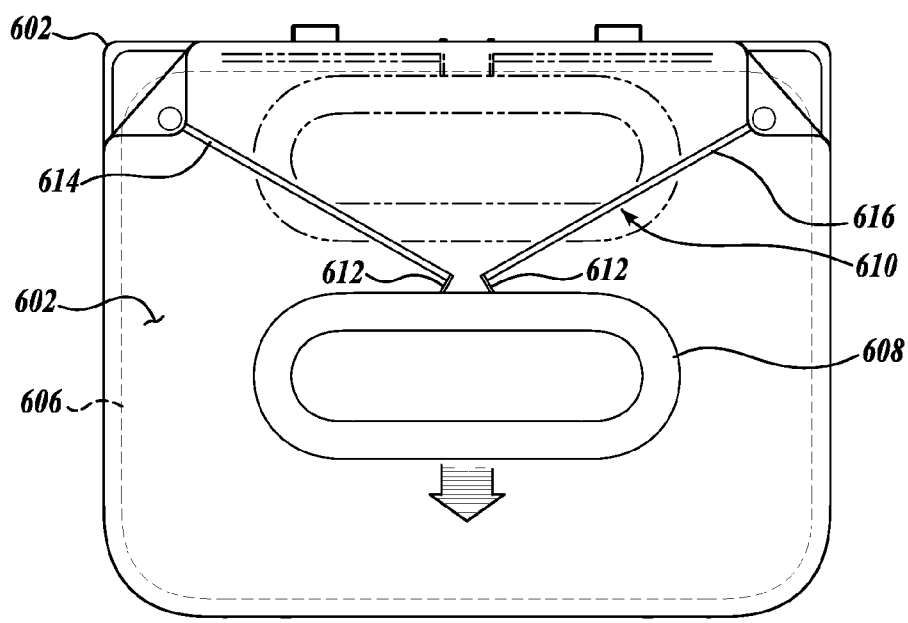
FIG. 10 depicts another perspective view of the embodiment of the system depicted in FIG. 9 with a pull force being exerted on the handle of the peelable lid.
Figure 11A:
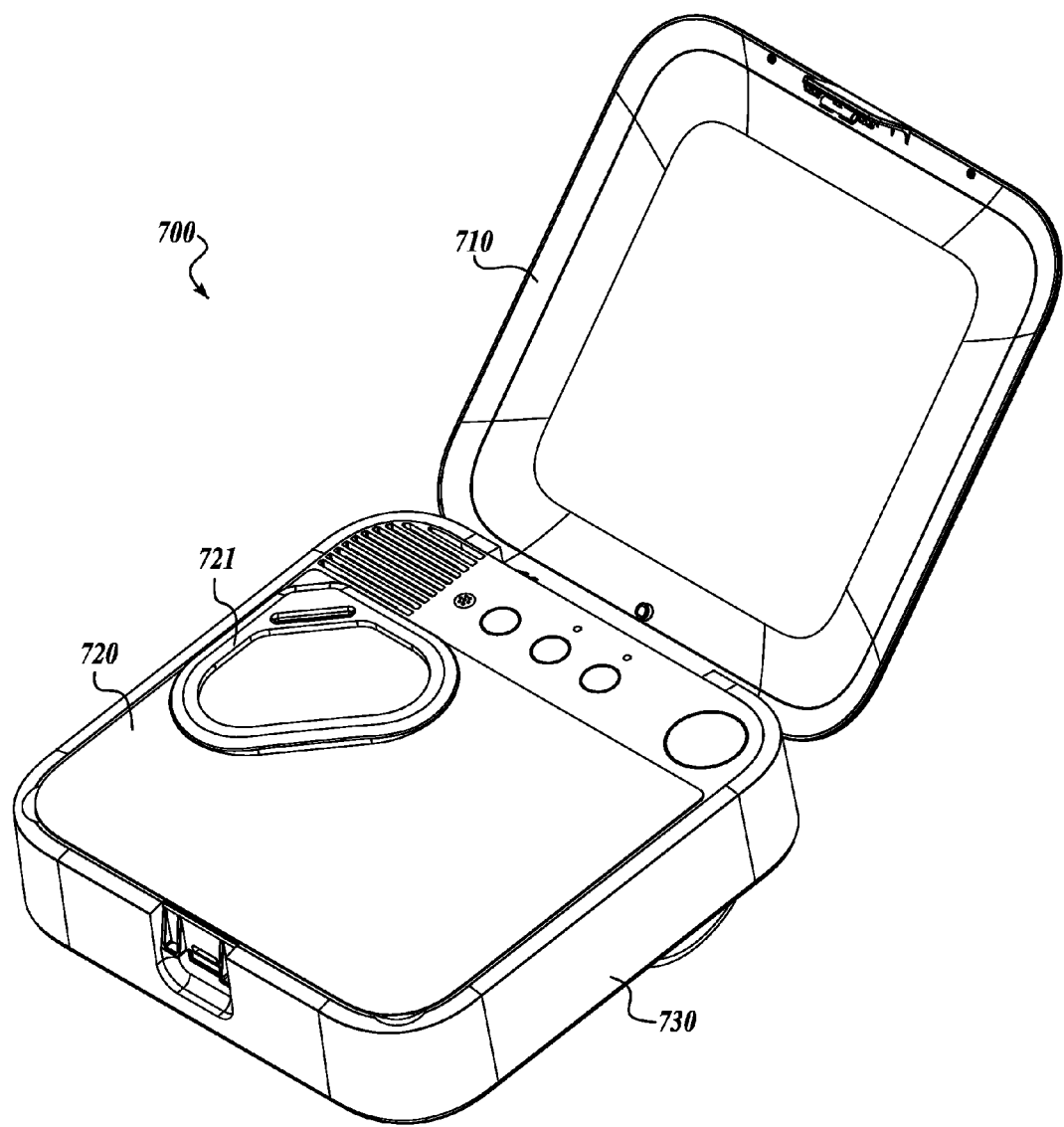
Figure 11B:
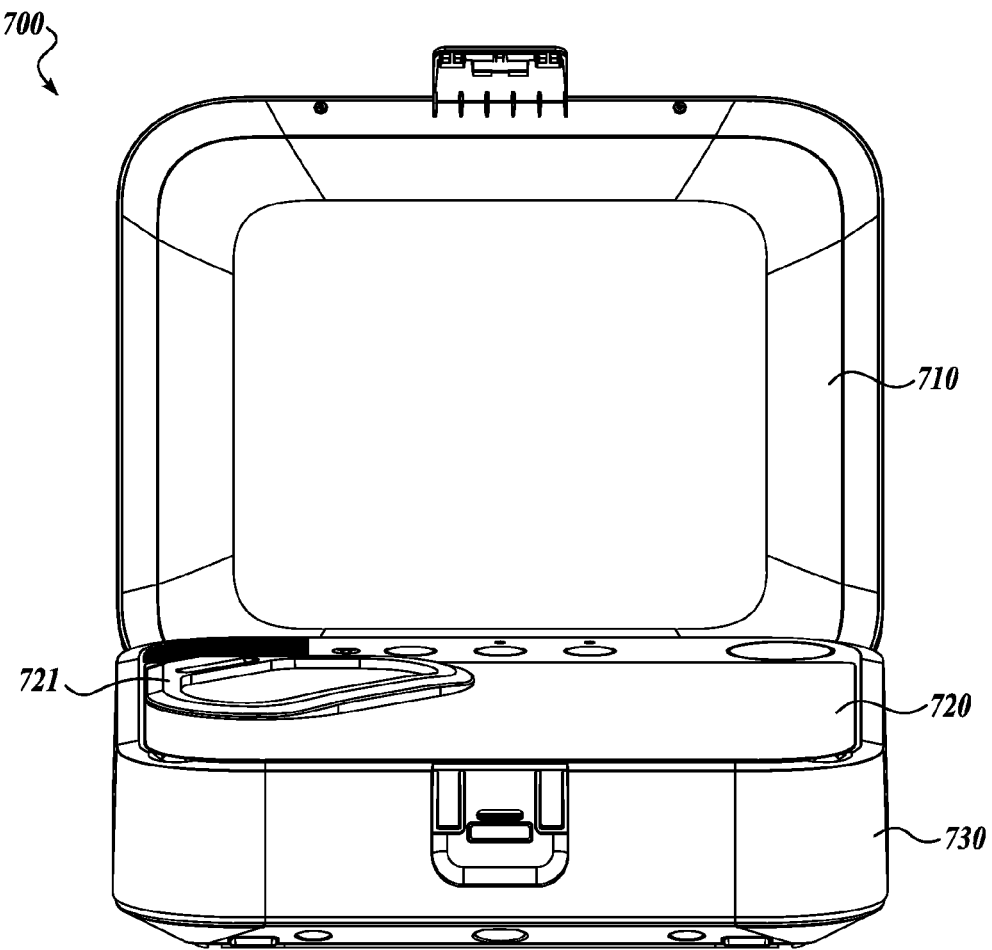
Figure 11C:
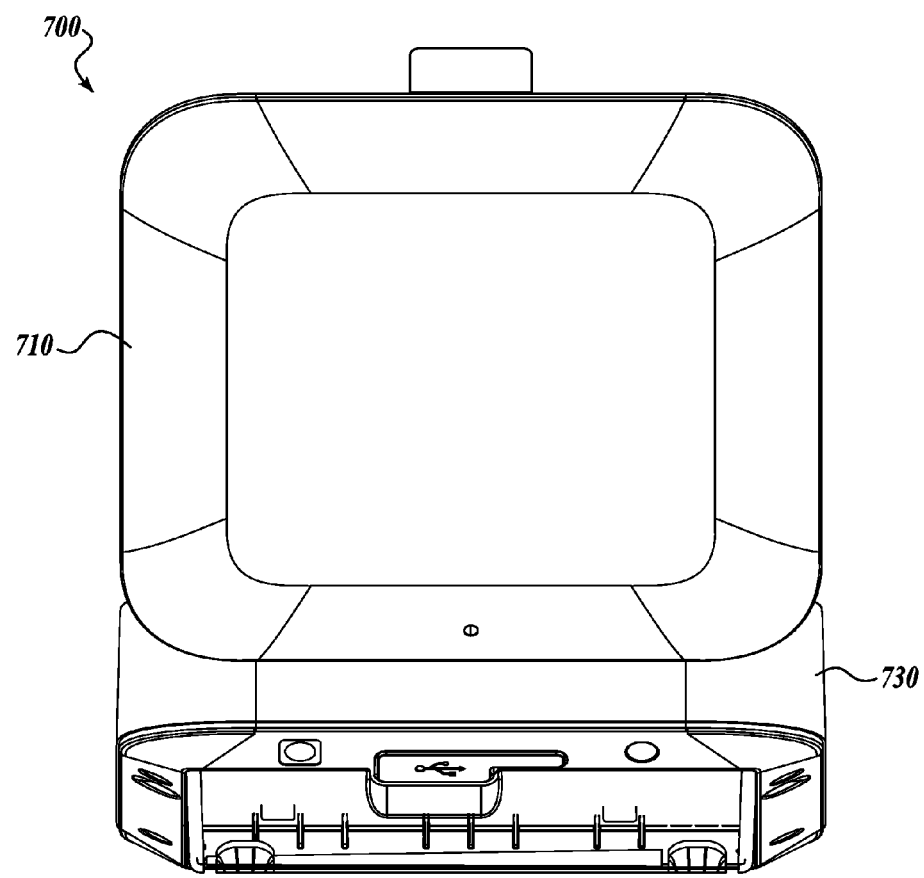
Figure 11D:
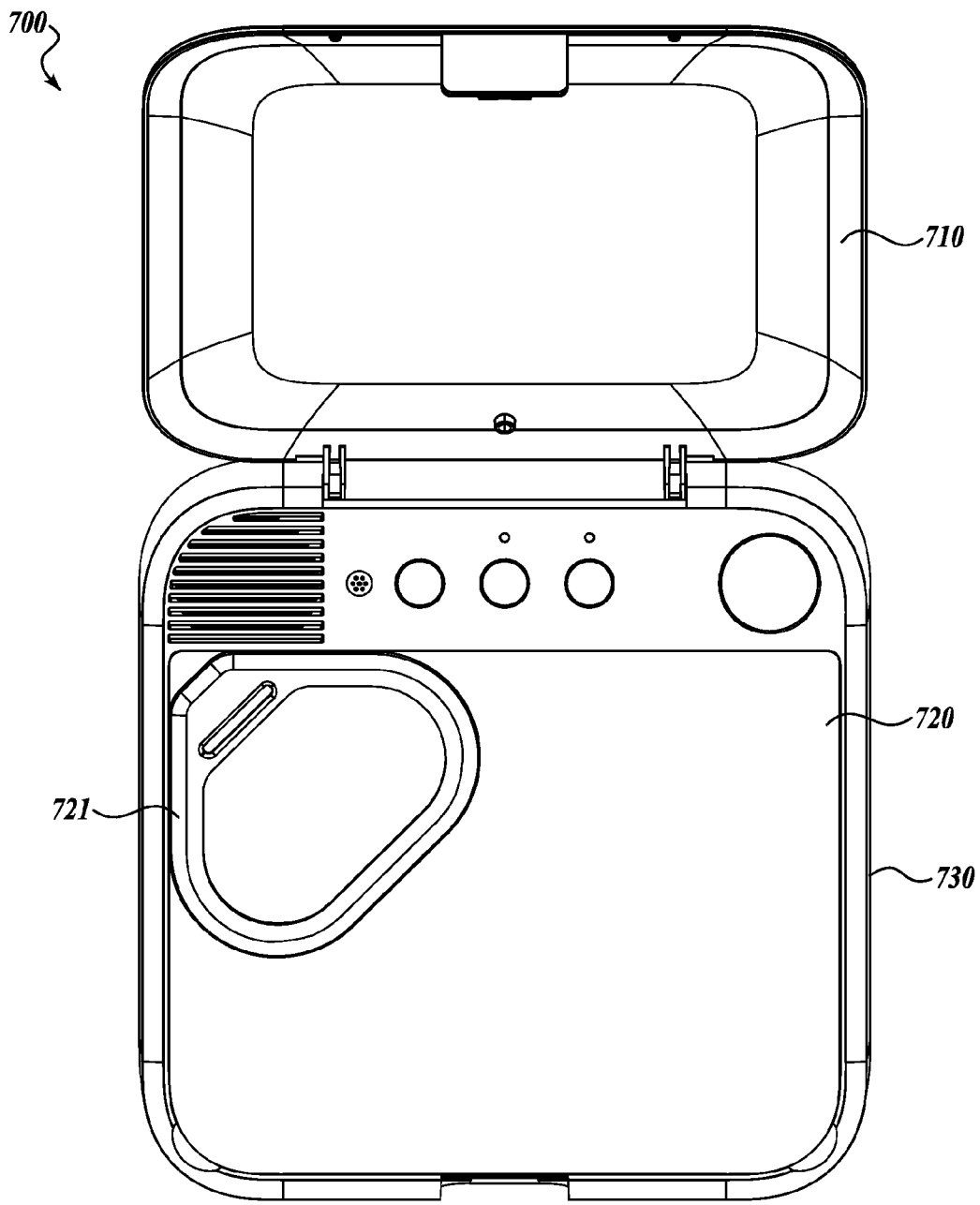
Figure 11E:
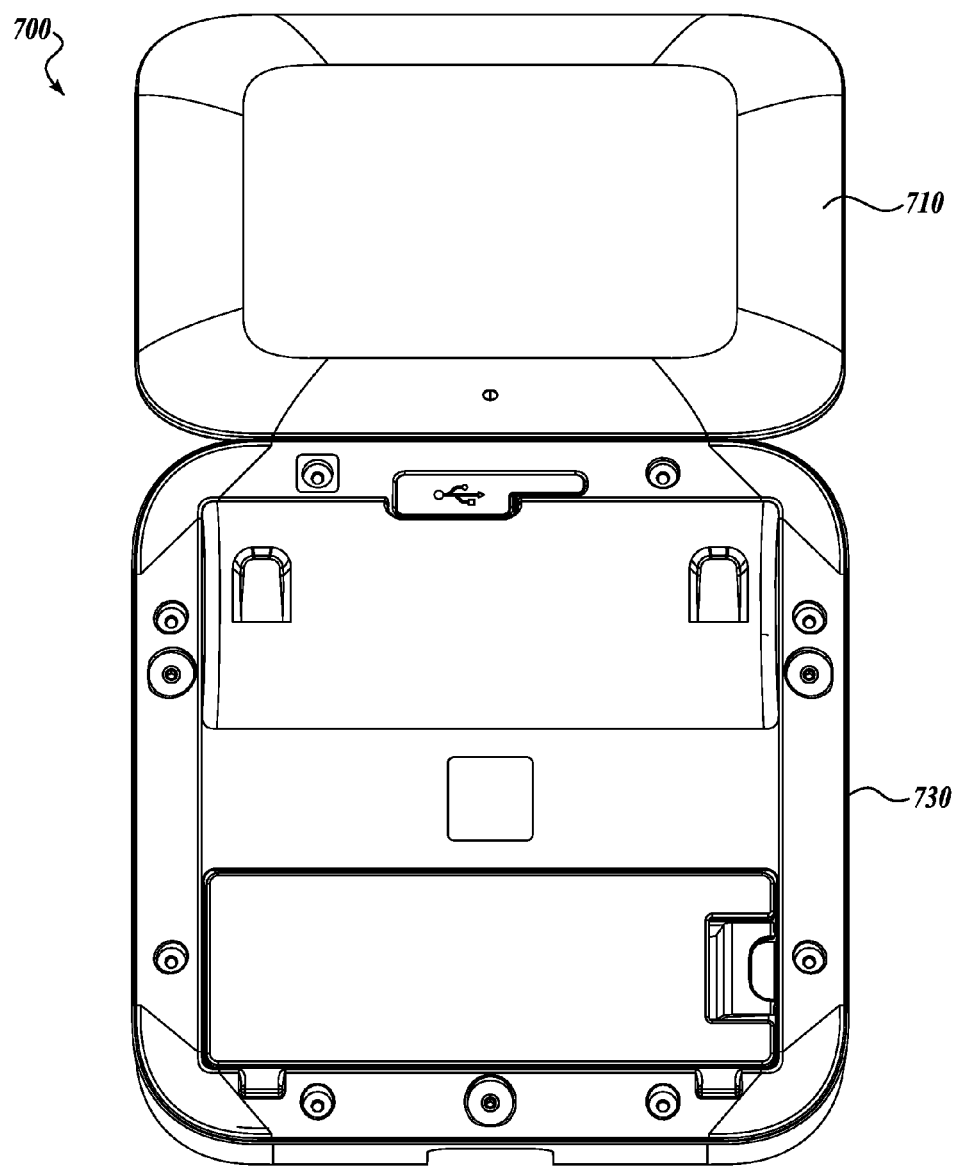
Figure 11F:
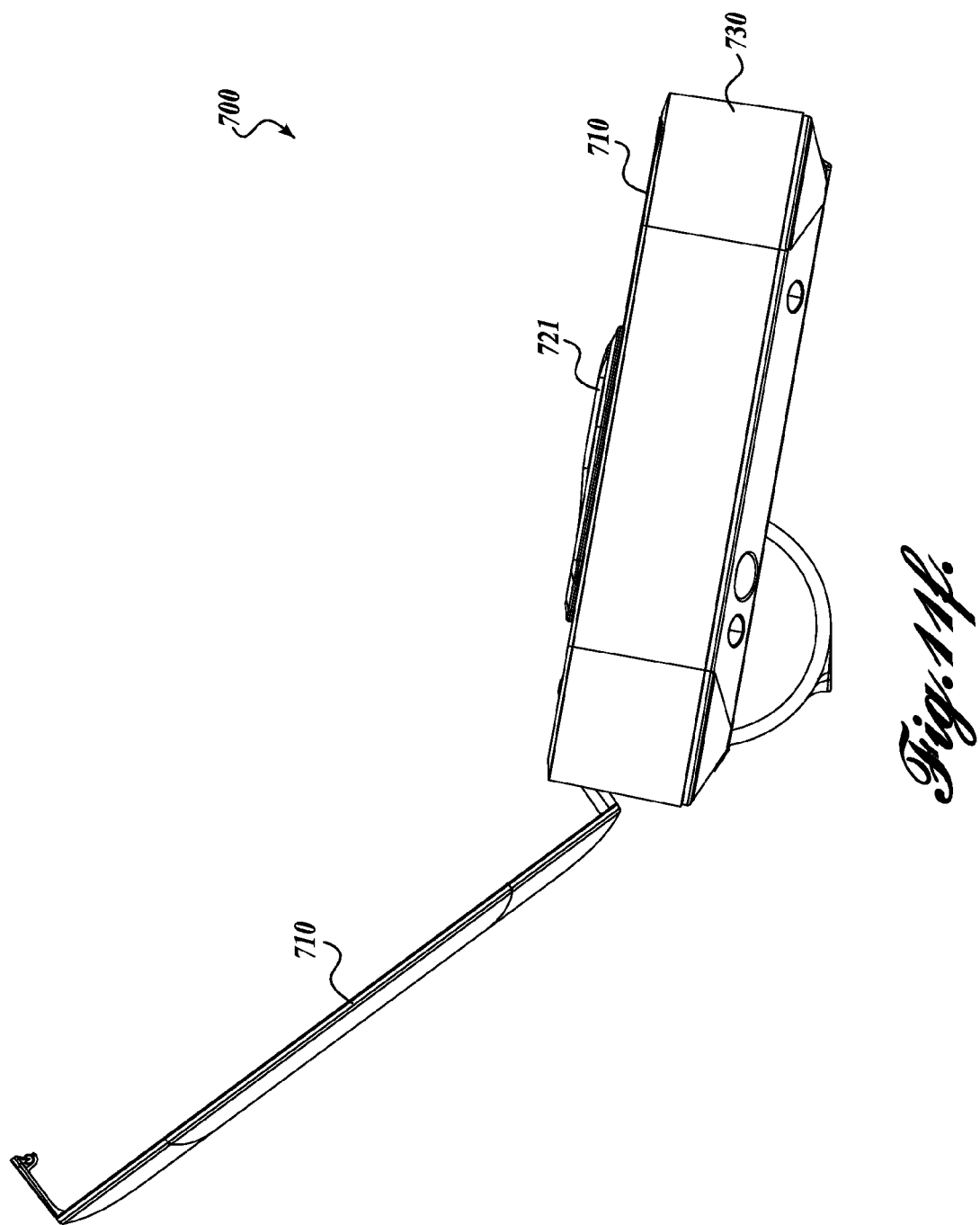
Figure 12A:
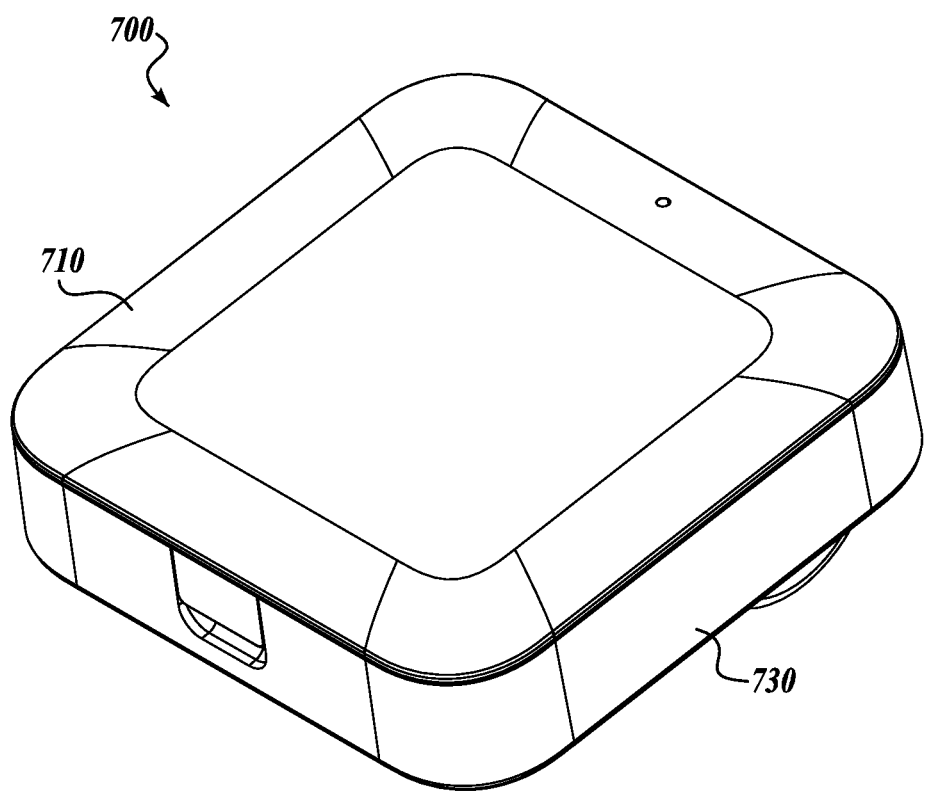
FIGS. 12A to 12G depict, respectively, a perspective view, a front view, a back view, a top view, a bottom view, a right side view, and a left side view of the embodiment of the AED from FIGS. 11A to 11G with the cover in a closed position.
Figure 12B:
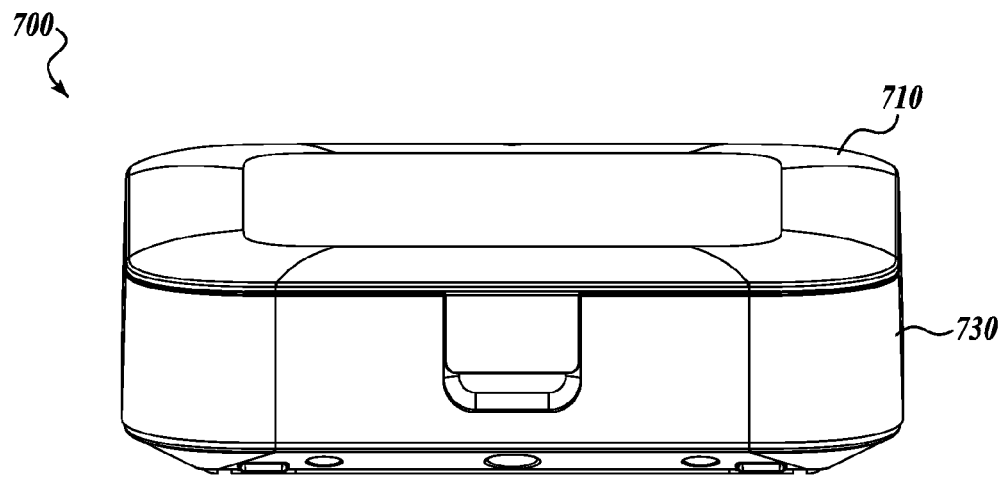
Figure 12C:
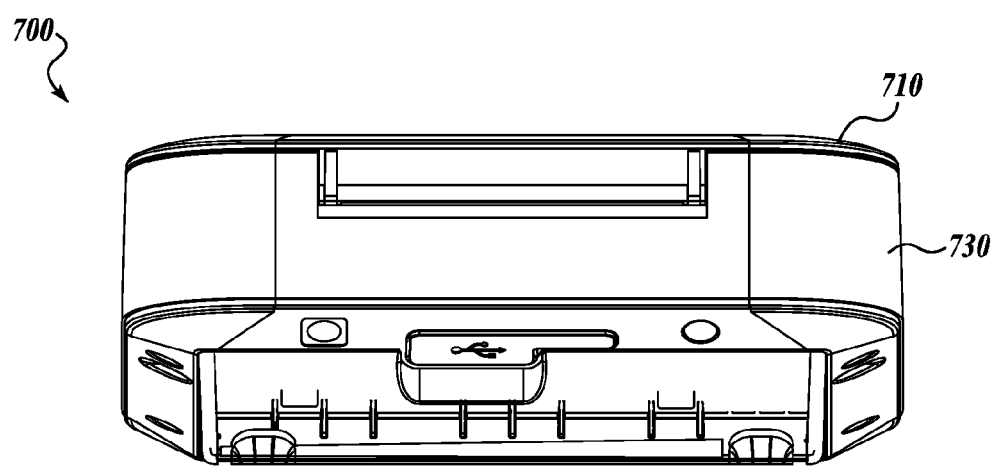
Figure 12D:
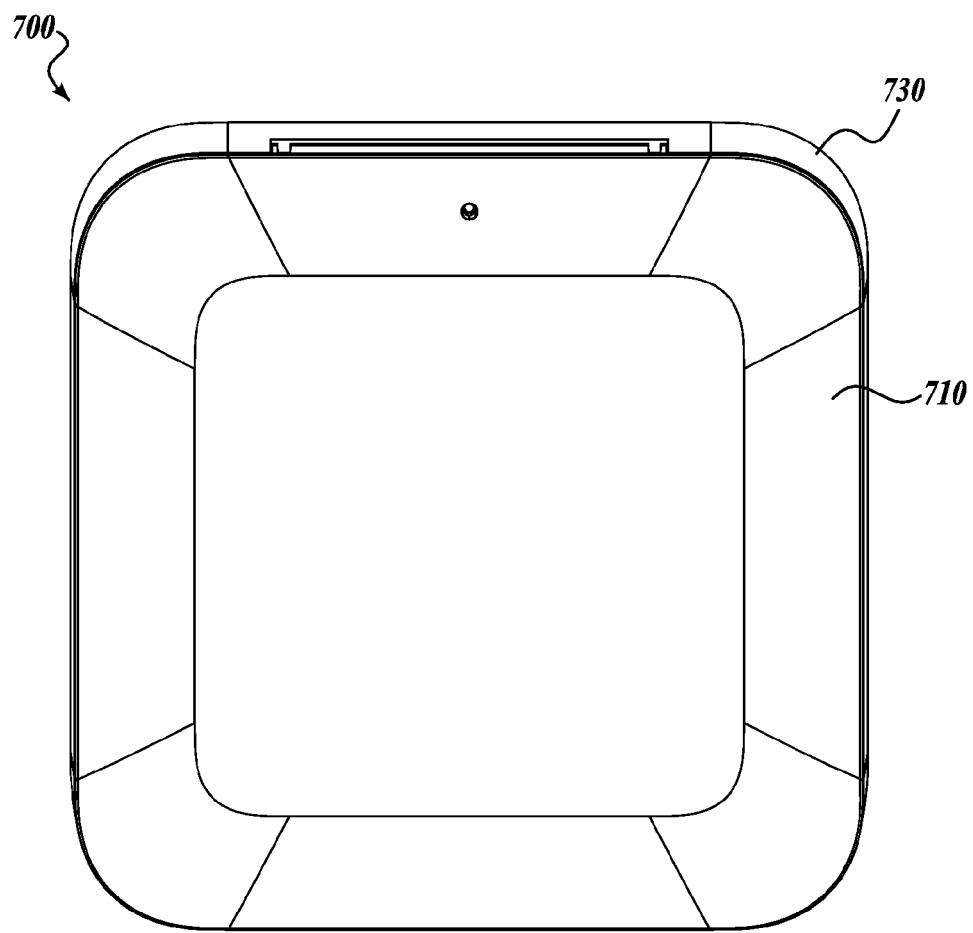
Figure 12E:
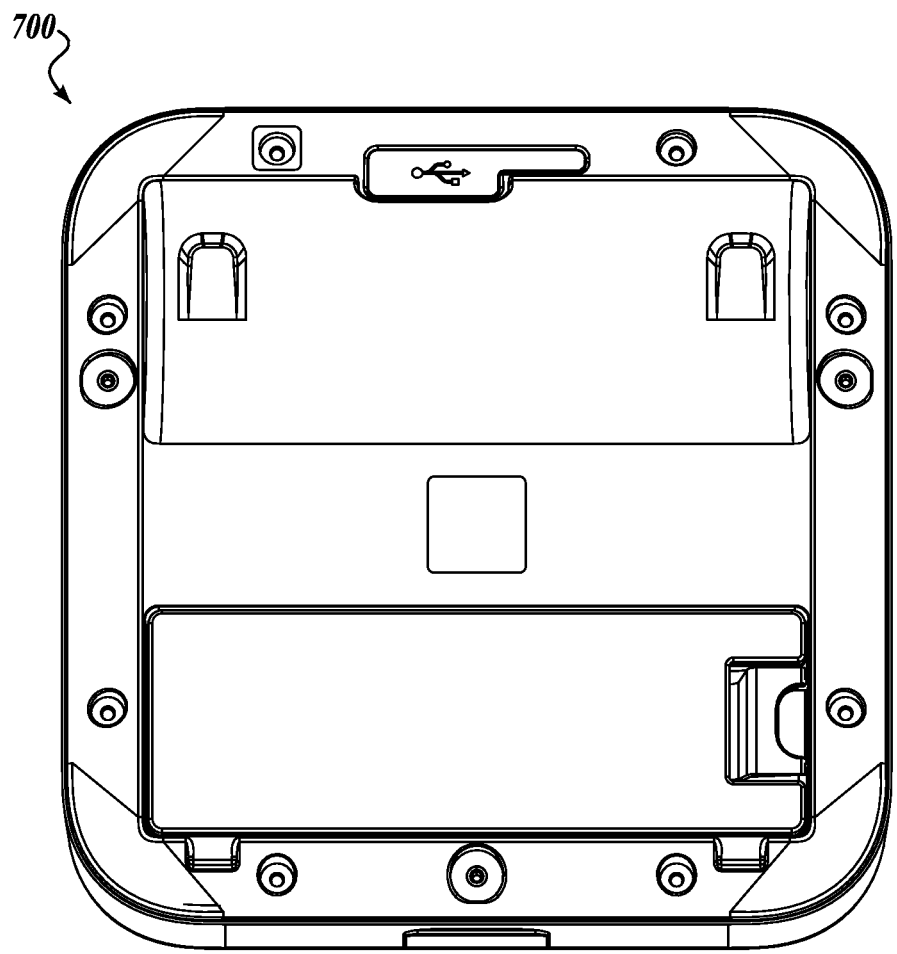
Figure 12F:
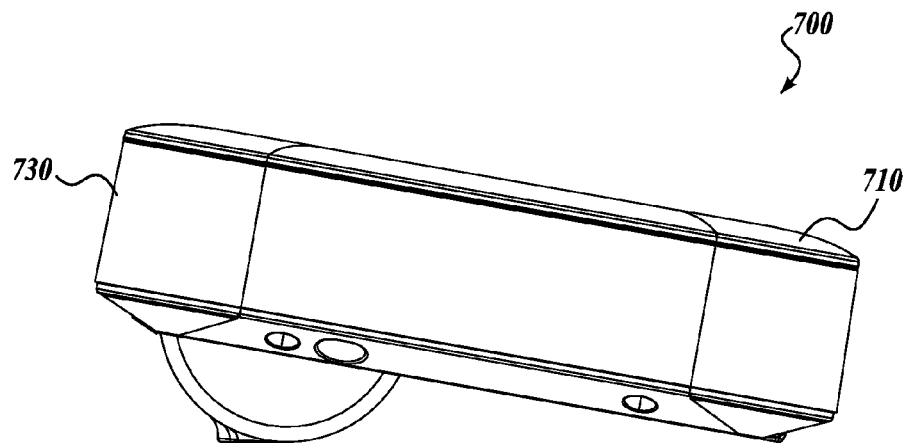
Figure 12G:
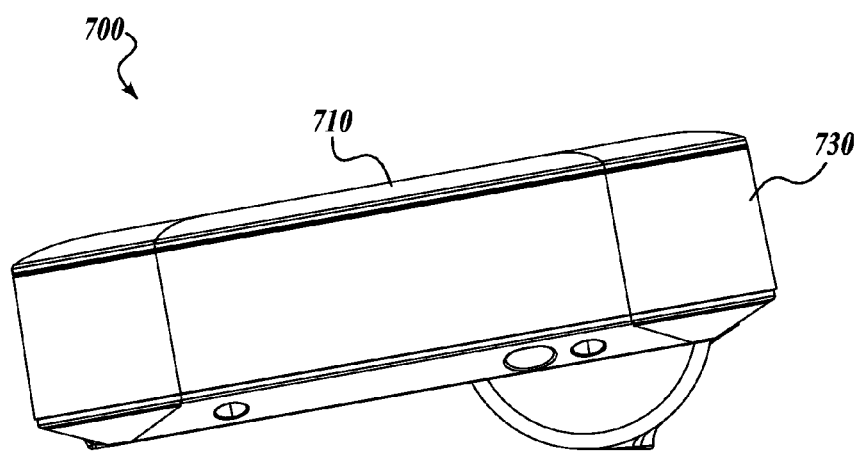
Figure 13A:
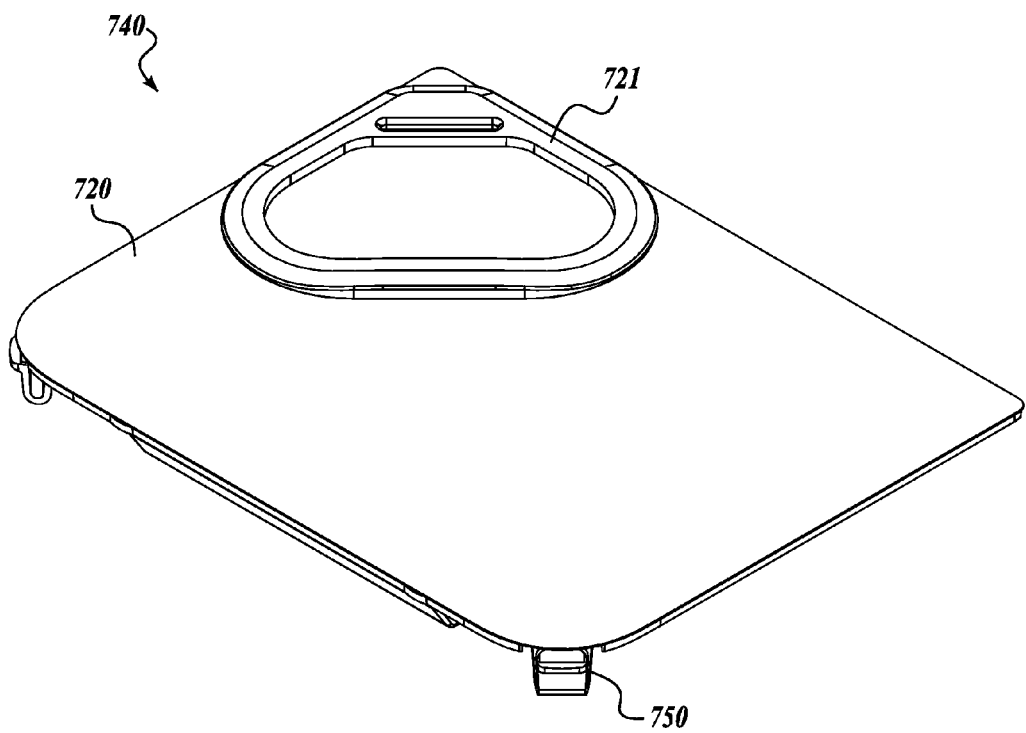
FIGS. 13A to 13G depict, respectively, a perspective view, a front view, a back view, a top view, a bottom view, a right side view, and a left side view of an electrode tray that can be used in an AED, such as the AED depicted in FIGS. 11A to 11G and FIGS. 12A to 12G.
Figure 13B:
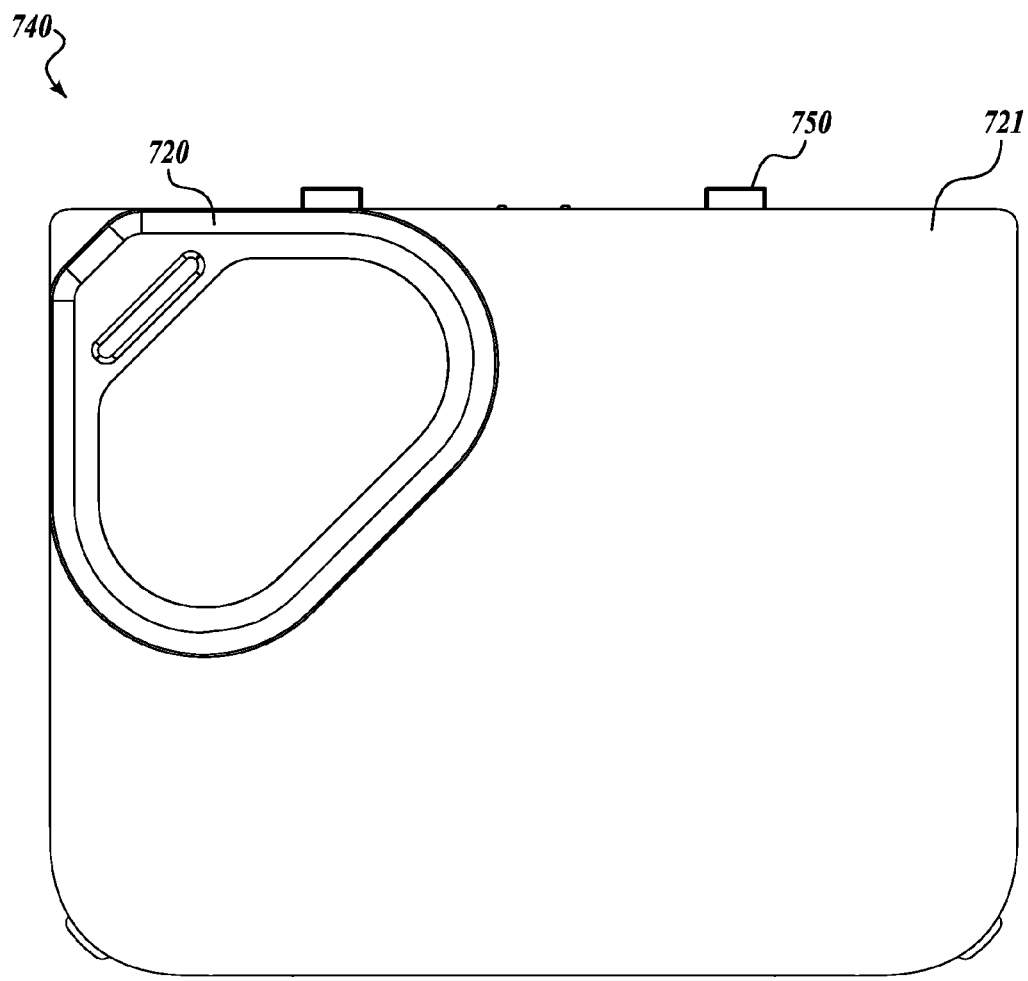
Figure 13C:
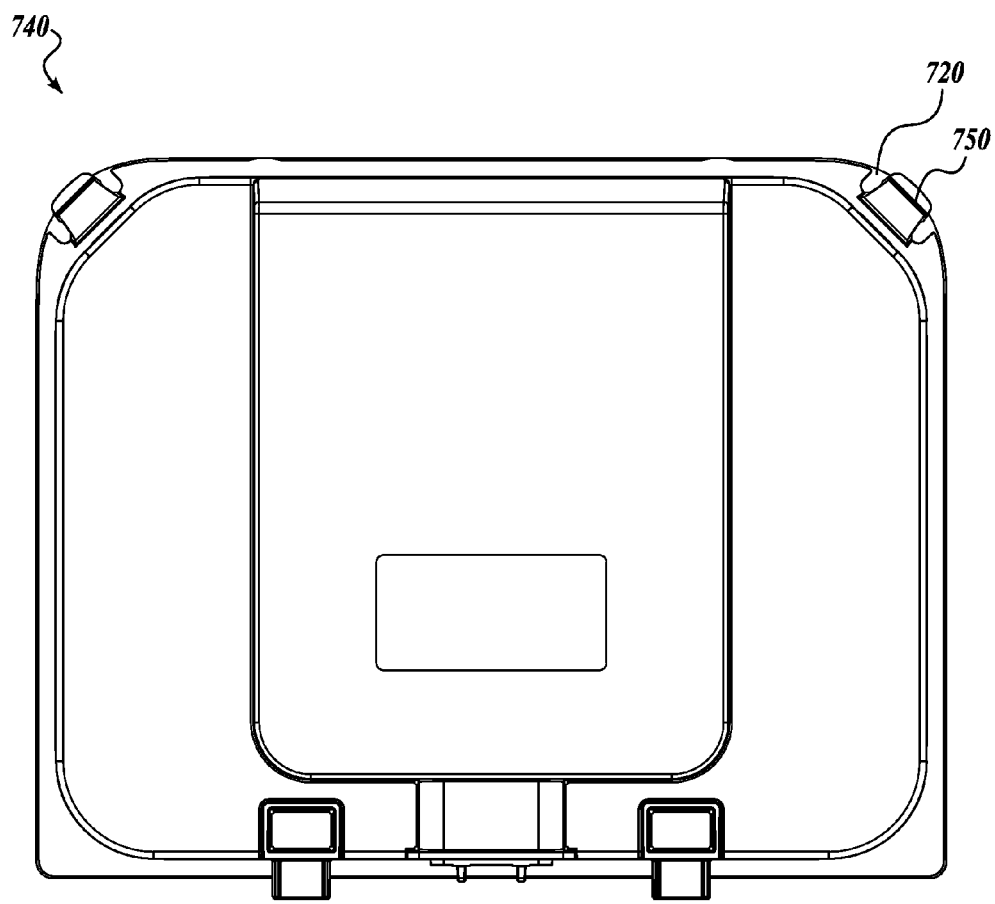
Figure 13D:
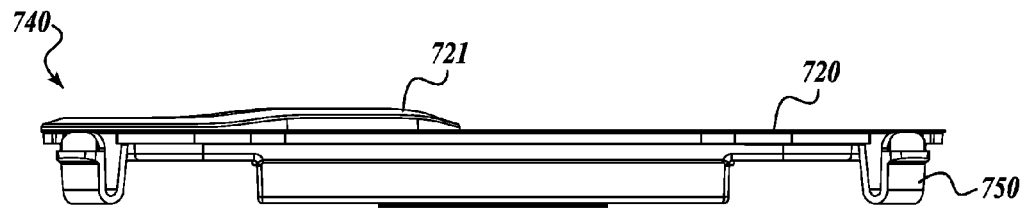
Figure 13E:
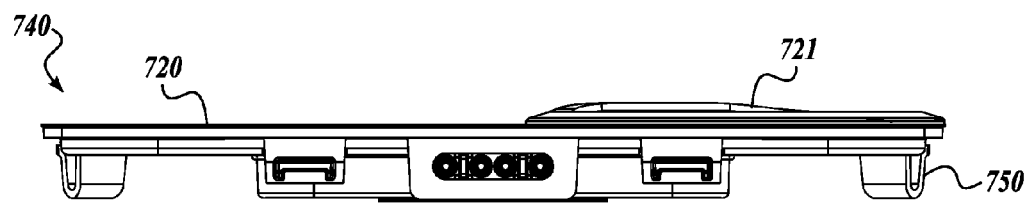
Figure 13F:
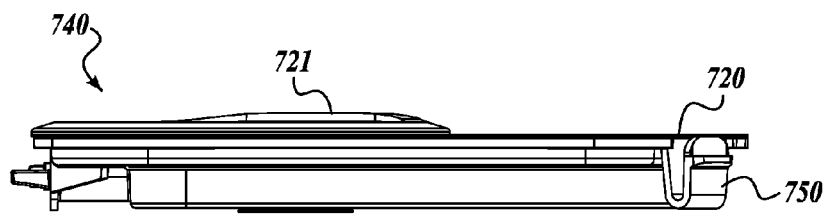
Figure 13G:
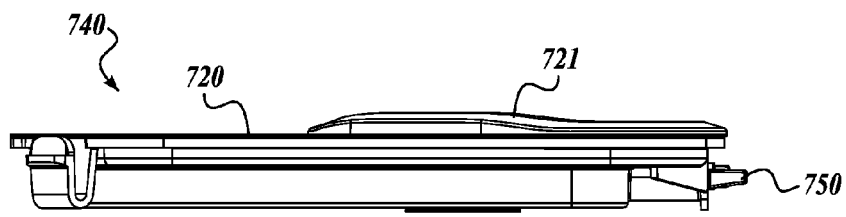

Another embodiment of a peelable lid system is depicted in FIGS. 9 and 10. A peelable lid 602 is sealed to a container 604 via a seal 606. A handle 608 and a lifting mechanism 610 are coupled to the lid 602. The lifting mechanism 610 is coupled to the lid 602 at a first attachment point 618 and a second attachment point 620. The lifting mechanism 610 is in the form of a three-bar linkage with a first link 614, a portion of the handle 608, and a second link 616. The first link 614 is coupled to the portion of the handle 608 via a first pivot joint 612 and the portion of the handle 608 is coupled to the second link 616 via a second pivot joint 612. The pivot joints 612 can be any type of pivot joints, such as hinges, compliant materials, and the like. The first link 614 and the second link 616 can be rigid or semi-rigid links. The portion of the handle 608 can operate as a third link to form a three-bar linkage with the first link 614 and the second link 616. Alternatively, a third link could be located between the first pivot joint 612 and the second pivot joint 612, and the handle 608 could be coupled to one of the first link 614, the second link 616, and the third link located between the pivot joints 612.

As depicted in FIG. 9, the first link 614 and the second link 616 in the lifting mechanism 610 can be substantially co-linear when the system is at rest (e.g., when no pull force is applied to the handle 608). As is depicted in FIG. 10, the lifting mechanism 610 can be configured such that, when a pull force is applied to the handle 608, the first link 616 rotates about the first pivot joint 612 to lift a first portion of the lid 602 and the second link 616 rotates about the second pivot joint 612 to lift a second portion of the lid 602. The lifted portions of the lid 602 can cause a pull force to be exerted on the seal 606 to begin breaking the seal 606 and to begin peeling the lid 602 away from the container 604. The three-bar linkage lifting mechanism 610 depicted in FIGS. 9 and 10 can operate is similar ways to the operation of the compliant mechanism lifting mechanism 112 depicted in FIGS. 1 and 4.

As mentioned above, peelable lids can be used to cover electrode trays of AEDs. FIGS. 11A to 11G and 12A to 12G depict various views of an embodiment of a design of an AED 700 that has a cover 710. More specifically, FIGS. 11A to 11G depict, respectively, a perspective view, a front view, a back view, a top view, a bottom view, a right side view, and a left side view of the AED 700 with the cover 710 in an opened position. FIGS. 12A to 12G depict, respectively, a perspective view, a front view, a back view, a top view, a bottom view, a right side view, and a left side view of the AED 700 with the cover 710 in a closed position.

With the cover 710 is in the opened position, as shown in FIGS. 11A to 11G, a peelable lid 720 that covers an electrode tray is depicted. The electrode tray can be located in a base portion 730 of the AED 700. To use the AED 700, a user can open the cover 710 by moving the cover 710 from the position shown in FIG. 12A to the position shown in FIG. 11A. At that point, the user can pull a handle 721 of the peelable lid 720. As described above, the peelable lid 720 can include a lifting mechanism that causes the pull force on the handle 720 to be transferred to at least two different locations where the peelable lid 720 is sealed to the electrode tray, increasing the likelihood that the entire peelable lid 720 can be removed by the user with a single pull of the handle 721. The user can continue pulling the handle 721 until the peelable lid 720 is removed from the electrode tray. The electrode tray can include electrode pads that can be applied to a patient's skin before performing treatment with the AED. Increasing the likelihood that the entire peelable lid 720 can be removed by the user with a single pull of the handle 721 can decrease the amount of time that a user spends preparing the patient for AED treatment and increase the probability that AED treatment will prevent permanent injury to or death of the patient.

FIGS. 13A to 13G depict, respectively, a perspective view, a front view, a back view, a top view, a bottom view, a right side view, and a left side view of an electrode tray 740 that can be used in an AED, such as the AED 700 depicted in FIGS. 11A to 11G and FIGS. 12A to 12G. The electrode tray 740 includes a tray 750 that is covered by the lid 720 with the handle 721.

It should be noted that for purposes of this disclosure, terminology such as "upper" and "lower," should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected" and "coupled," and variations thereof herein are used broadly and encompass direct and indirect connections and couplings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

What is claimed is:

1. An electrode assembly for use with a defibrillator, the assembly comprising:
    a tray adapted to be fit into or on a defibrillator;
    at least one electrode pad disposed in the tray;
    a peelable lid configured to cover an opening of the tray;
    a seal disposed between the tray and the peelable lid;
    a handle coupled to the peelable lid; and
    a lifting mechanism coupled to handle and the peelable lid, wherein the lifting mechanism is coupled to the peelable lid via a plurality of attachment points.

2. The electrode assembly of claim 1, wherein the plurality of attachment points comprises a first attachment point coupled to a first corner of the peelable lid and a second attachment point coupled to a second corner of the peelable lid.

3. The electrode assembly of claim 2, wherein the handle is coupled to a side of the peelable lid between the first corner and the second corner of the peelable lid.

4. The electrode assembly of claim 3, wherein the lifting mechanism is configured such that, in response to the pull force applied to the handle, the first attachment point and the second attachment point are biased away from the container to curl a side of the peelable lid between the first corner and the second corner.

5. The electrode assembly of claim 1, wherein at least one of the plurality of attachment points is coupled to the peelable lid near a corner of the peelable lid.

6. The electrode assembly of claim 5, wherein the seal comprises a corner near the corner of the peelable lid, wherein at least one portion of the peelable lid is lifted by the at least one of the plurality of attachment points at the corner of the peelable lid, and wherein the corner of the seal is broken when the corner of the peelable lid is lifted by the at least one of the plurality of attachment points.

7. The electrode assembly of claim 6, wherein the corner of the seal comprises one of a rounded corner or a square corner.

8. The electrode assembly of claim 1, wherein the seal comprises one or more of an adhesive, glue, epoxy, a mechanical bond, or a polymer bond.

9. The electrode assembly of claim 1, wherein, in response to a pull force being applied to the handle, the lifting mechanism is configured to lift at least one portion of the peelable lid near each of the plurality of attachment points.

10. The electrode assembly of claim 1, wherein at least one of the plurality of attachment points is coupled to the peelable lid a distance away from the handle.

11. The electrode assembly of claim 1, wherein the peelable lid has a round shape, and wherein the seal is round.

12. The electrode assembly of claim 1, wherein the lifting mechanism is configured to transfer a pull force that is applied to the handle to the seal in at least two different locations.

13. The electrode assembly of claim 1, wherein the lifting mechanism is configured to transfer a pull force that is applied to the handle to at least a first location and a second location along the seal, and wherein the pull force is transferred to the seal at the first location in a first direction that is different from a second direction of the pull force transferred to the seal at the second location.

14. The electrode assembly of claim 13, wherein the first direction is substantially perpendicular to a side of the peelable lid, and wherein the second direction is not substantially perpendicular to the side of the peelable lid.

15. The electrode assembly of claim 1, wherein the peelable lid comprises one or more layers, and wherein the one or more layers include at least one of a paper layer, a wax layer, a metallic foil, or a polymer film.

* * * * *